US006982519B2

(12) United States Patent
Guillorn et al.

(10) Patent No.: US 6,982,519 B2
(45) Date of Patent: Jan. 3, 2006

(54) INDIVIDUALLY ELECTRICALLY ADDRESSABLE VERTICALLY ALIGNED CARBON NANOFIBERS ON INSULATING SUBSTRATES

(75) Inventors: Michael A. Guillorn, Knoxville, TN (US); Timothy Eric McKnight, Greenback, TN (US); Vladimir I. Merkulov, Knoxville, TN (US); Anatoli Vasilievich Melechko, Knoxville, TN (US); Michael Leon Simpson, Knoxville, TN (US)

(73) Assignee: UT-Battelle LLC, Oak Ridge, TN (US)

( * ) Notice: Subject to any disclaimer, the term of this patent is extended or adjusted under 35 U.S.C. 154(b) by 364 days.

(21) Appl. No.: 09/964,270

(22) Filed: Sep. 26, 2001

(65) Prior Publication Data

US 2003/0052585 A1 Mar. 20, 2003

Related U.S. Application Data

(60) Provisional application No. 60/322,929, filed on Sep. 18, 2001.

(51) Int. Cl.
*H01J 1/05* (2006.01)
*H01J 1/14* (2006.01)
*H01J 19/06* (2006.01)

(52) U.S. Cl. .................. 313/311; 313/309; 313/336; 313/351

(58) Field of Classification Search ............... 313/311, 313/310, 309, 459, 351; 438/548, 595, 612
See application file for complete search history.

(56) References Cited

U.S. PATENT DOCUMENTS 5,806,181 A * 9/1998 Khandros et al. ............. 29/874

6,110,823 A * 8/2000 Eldridge et al. ............ 438/660
6,336,269 B1 * 1/2002 Eldridge et al. ............. 29/885
6,649,431 B2 * 11/2003 Merkulov et al. ............ 438/20
6,692,324 B2 * 2/2004 Simpson et al. ............. 445/24

OTHER PUBLICATIONS

Guillom, et al., "Operation of a gated field emitter using an individual carbon nanofiber cathode," Applied Physics Letters, vol. 79, No. 21, pp. 3506-3508, Nov. 19, 2001.
Baylor, et al., "Field emission from isolated individual vertically aligned carbon nanocones" Journal of Applied Physics, vol. 91, No. 7, pp. 4602-4606, Apr. 1, 2002.
Yahachi et al., "Field Emission Patterns from Single-Walled Carbon Nanotubes," Japan Journal Applied Physics, vol. 36, pp. 1340-1342, Oct. 1, 1997.
Matsumoto, et al., "Ultralow biased field emitter using single-wall carbon nanotube directly grown onto silicon tip by thermal chemical vapor deposition," Applied Phyics Letters, vol. 78, No. 4, pp. 539-540, Jan. 22, 2001.
Guillom,et al., "Fabrication of gated cathode structures using an in situ grown vertically aligned carbon nanofiber as a field emission element", Journal of Vacuum Science, pp. 573-578, Mar./Apr. 2001.

(Continued)

*Primary Examiner*—Joseph Williams
*Assistant Examiner*—Kevin Quarterman
(74) *Attorney, Agent, or Firm*—John Bruckner, PC (57) ABSTRACT

Systems and methods are described for individually electrically addressable carbon nanofibers on insulating substrates. An apparatus includes an electrically conductive interconnect formed on at least a part of an insulating surface on a substrate; and at least one vertically aligned carbon nanofiber coupled to the electrically conductive interconnect. A kit includes a substrate having an insulating surface; an electrically conductive interconnect formed on at least a part of the insulating surface; and at least one vertically aligned carbon nanofiber coupled to the electrically conductive interconnect.

25 Claims, 6 Drawing Sheets

OTHER PUBLICATIONS

Rinzier, et al., "Unraveling Nanotubes: Field Emission from an Atomic Wire" available at www.jstor.org, pp. 1550-1553, May 9, 2002.

Merkulov, et al., "Patterned grown of individual and multiple vertically aligned carbon nanofibers," Applied Physics Letters, vol. 76, No. 24, pp. 3555-3557, Jun. 12, 2000.

Xueping, et al., "A method for fabricating large-area, patterned, carbon nanotube field emitters," Applied Physics Letters, vol. 74, No. 17, pp. 2549-2551, Apr. 26, 1999.

Merkulov, et al., "Scanned-probe field-emission studies of vertically aligned carbon nanofibers" Journal of Applied Physics, vol. 89, No. 3, pp. 1933-1937, Feb. 1, 2001.

Bonard, et all, "Field emission from single-wall carbon nanotube films" Applied Physics Letters, vol. 73, No. 7, pp. 918-920, Aug. 17, 1998.

Xueping, et al., "Carbon Nanotube-based vacuum microelectronic gated cathode," Material Research Society Symposium, vol. 509, pp. 107-109.

Dean, eta l., "The environmental stability of field emission from single-walled carbon nanotubes" Applied Physics Letters, vol. 75, No. 19, pp. 3017-3019.

Wang, et al., "Flat panal display prototype using gated carbon nanotube field emitters," Applied Physics Letters, vol. 78, No. 9, pp. 1294-1296, Feb. 26, 2001.

Lee, et al., "Realization of Gated Field Emitters for Electrophotonic Applications Using Carbon Nanotube Line Emitters Directly Grown into Submicrometer Holes," Advanced Materials Communications, vol. 13, No. 7, pp. 479-482, Arp. 4, 2001.

Gullorn, et al. "Microfabricated field emission devices using carbon nanofibers as cathode elements", Journal of Vaccuum Science Technology B19(6), pp. 2598-2601, Nov./Dec. 2001.

* cited by examiner

INDIVIDUALLY ELECTRICALLY ADDRESSABLE VERTICALLY ALIGNED CARBON NANOFIBERS ON INSULATING SUBSTRATES

CROSS-REFERENCE TO RELATED APPLICATION

This application is related to and claims a benefit of priority under 35 U.S.C. 119(e) and/or 35 U.S.C. 120 from, U.S. Ser. No. 60/322,929, filed Sep. 18, 2001, now pending, the entire contents of which are hereby expressly incorporated by reference for all purposes.

STATEMENT AS TO RIGHTS TO INVENTIONS MADE UNDER FEDERALLY-SPONSORED RESEARCH AND DEVELOPMENT

This invention was made with United States Government support under contract to UT-Battelle, LLC. The Government has certain rights in this invention.

BACKGROUND OF THE INVENTION

1. Field of the Invention

The invention relates generally to the fields of materials and nanotechnology. More particularly, the invention relates to at least one fiber on an electrically conductive interconnect located on an insulating surface of a substrate. Specifically, a preferred implementation of the invention relates to a plurality of individually electrically addressable vertically aligned carbon nanofibers that are grown by DC plasma enhanced chemical vapor deposition on the electrically conductive interconnect. The invention thus relates to vertically aligned carbon nanofibers of the type that can be termed individually electrically addressable.

2. Discussion of the Related Art

Nanostructured graphitic carbon-based materials are among the most promising candidates for microfabricated cold cathode FE devices such as parallel electron sources for electron microscopy, electron beam lithography and FE flat panel displays. The FE properties of the VACNF have been studied in detail and demonstrate that the VACNFs behave as robust FE cathodes. In order to make full use of the VACNF in FE devices a way to individually electrically contact the base of the VACNF is required. This allows a way to precisely control the emitted current through a single VACNF during device operation.

VACNFs are produced in a DC plasma enhanced chemical vapor deposition (PECVD) process. Aspects of this synthesis process require an electrostatic potential to be placed on the substrate material from which the VACNFs are to be grown. As a consequence, it is not possible to produce individual VACNFs on substrates that are not electrically conductive. This presents several problems for creating arrays of VACNFs that are individually electrically addressable. A means of creating such arrays on insulating substrates is essential for realizing practical VACNF-based FE devices. However, no process has currently been reported that can achieve this goal.

Electrical and electrochemical methods for characterizing small volumes are a critical need in many fields of study including semiconductor manufacture (device characterization and defect detection), materials science (composition, corrosion, and interface characterization), and biology and biotechnology (intra- and extracellular molecular probing, electrophysiology). To create probing devices with improved spatial resolution that can accurately characterize these mesoscale phenomena, it is necessary to fabricate probes with nanoscale electrically (and electrochemically) active probe tips. Moreover, to achieve the highest sensing resolution possible, fabrication process for such probes should offer a means to deterministically control the active surface area (and thus probing volume) at the tip of the device.

In recent years, a large research effort has focused on the development of microelectrode electrochemical probes for probing small volumes at fluid/material interfaces and within and around biological cells. The promise of these electrodes lies in their fast response times (ms time scale), high mass sensitivity (zeptomole, i.e. 100–1000 molecules), small size, large linear dynamic range (up to 4 orders of magnitude) and selectivity, and because molecules of interest can be followed without the need for derivatization as is necessary in fluorescence microscopy. The microelectrodes reported to date for small volume analysis typically consist of a linear carbon nanotube bundle surrounded by an insulating layer of glass. Macroscopic carbon bundles are placed into glass capillary tubes, which are then pulled down to microscale dimensions (0.5 to 10 $\mu$m). Microscopic inspection allows the cleaving of the pulled capillary in the vicinity of the entrained carbon bundle, providing a conductive carbon tip, surrounded by an insulating sheath of glass. In electrolyte systems, the resultant microelectrode can be placed in close proximity to a region of interest, and used to analyze the local microenvironment for a large variety of electroactive species, such as galvanic corrosion species (in materials science applications) and many biological compounds. For easily oxidizable substances, i.e., catecholamines, indoleamines, oxygen, and doxorubicin, the native carbon electrode surface is sufficient for electrochemical analysis and these substances have been readily detected in or near the surface of single cells. In fact these electrodes, at present, are one of only a few available techniques to measure the exocytotic release of neurotransmitters from single cells.

The small size of these electroanalytical probes provides obvious advantages in terms of application and placement of the electrode at or within very small volumes and for measuring the spatial and temporal dynamics of electrochemically active species within small scale systems. The probing volume of an individual probe is defined by the electrochemical boundary layer of the electrode, which is typically a region consisting of a 10 nm radial distance from the electrode surface. Therefore, the small electroactive surface area of an electrochemical microelectrode provides for the ability to probe very small regions of interest, and to obtain quantitative information of a measured molecular species within extremely localized volumetric regions. The small size also provides many advantages in terms of the electrochemistry involved. Perhaps most significant is that the reduction in electrochemically active surface area results directly in a reduction of the double layer capacitance that exists at the interface between any electrode/electrolyte system. This improves the ratio of faradaic to non-faradaic (or 'charging') current at the electrode and thus increases the signal to noise ratio of most electroanalytical techniques. The reduction in capacitance also provides for more rapid electroanalysis to be conducted within the region of interest due to the resultant decrease in background or charging current that plagues larger electrode systems. The reduced electrode surface area also reduces the overall currents generated between electrodes during electroanalytical events, and thus greatly reduces the amount of potentially interfering products that are generated during electroanalysis that might otherwise have deleterious effects on the local environment. Thus, electroanalysis at ultramicroelectrodes provides for the ability to monitor molecular events, while generating minimal perturbation to the system during the measurement.

While microelectrodes reported in the literature have allowed unprecedented spatial and temporal measurements to be made within small volumes, the electrodes themselves are still rather large compared to the size of many targeted systems (i.e. biological cells and nanoscale material interfaces). They are also monolithic, single electrode components, therefore spatial mapping of species in and around a system requires physically moving either the analyzed system or the electrode. The fabrication process of individual probes is also quite arduous, requiring the selection of carbon fiber bundles, placement in a capillary, pulling the capillary, cleaving, polishing, and interconnecting to macroscopic analysis instruments. As a consequence, there is a high degree of variation from probe to probe, due to differences in the fabrication process, in addition to the electrochemical behavior of the raw materials.

SUMMARY OF THE INVENTION

There is a need for the following embodiments. Of course, the invention is not limited to these embodiments.

According to an aspect of the invention, a method comprises: forming an electrically conductive interconnect on at least a part of an insulating surface on a substrate; and growing at least one fiber that is coupled to the electrically conductive interconnect. According to another aspect of the invention, an apparatus comprises: an electrically conductive interconnect formed on at least a part of an insulating surface on a substrate; and at least one fiber coupled to the electrically conductive interconnect. According to another aspect of the invention, a kit comprises: a substrate having an insulating surface; an electrically conductive interconnect formed on at least a part of the insulating surface; and at least one fiber coupled to the electrically conductive interconnect.

These, and other, embodiments of the invention will be better appreciated and understood when considered in conjunction with the following description and the accompanying drawings. It should be understood, however, that the following description, while indicating various embodiments of the invention and numerous specific details thereof, is given by way of illustration and not of limitation. Many substitutions, modifications, additions and/or rearrangements may be made within the scope of the invention without departing from the spirit thereof, and the invention includes all such substitutions, modifications, additions and/or rearrangements.

BRIEF DESCRIPTION OF THE DRAWINGS

The drawings accompanying and forming part of this specification are included to depict certain aspects of the invention. A clearer conception of the invention, and of the components and operation of systems provided with the invention, will become more readily apparent by referring to the exemplary, and therefore nonlimiting, embodiments illustrated in the drawings, wherein like reference numerals designate the same elements. The invention may be better understood by reference to one or more of these drawings in combination with the description presented herein. It should be noted that the features illustrated in the drawings are not necessarily drawn to scale.

DESCRIPTION OF PREFERRED EMBODIMENTS

The invention and the various features and advantageous details thereof are explained more fully with reference to the nonlimiting embodiments that are illustrated in the accompanying drawings and detailed in the following description. Descriptions of well known starting materials, processing techniques, components and equipment are omitted so as not to unnecessarily obscure the invention in detail. It should be understood, however, that the detailed description and the specific examples, while indicating preferred embodiments of the invention, are given by way of illustration only and not by way of limitation. Various substitutions, modifications, additions and/or rearrangements within the spirit and/or scope of the underlying inventive concept will become apparent to those skilled in the art from this disclosure.

The below-referenced U.S. Patents disclose embodiments that were satisfactory for the purposes for which they are intended. U.S. Pat. No. 6,020,747, entitled electrical contact probe, discloses fibers mechanically attached to a substrate. U.S. Pat. No. 6,146,227, entitled method for manufacturing carbon nanotubes as functional elements of MEMS devices, discloses catalytic growth in nanoscale holes that are used to hold catalyst for subsequent growth of individual and arrays of tubes; the holes are disclosed to be fabricated in a MEMS layer via electrochemical and photoelectrochemical etching. U.S. Pat. No. 6,239,547, entitled electron emitting source and method of manufacturing the same, discloses affixing carbon nanotubes to a conductive substrate using a conductive adhesive such that carbon tip is still exposed. U.S. Pat. No. 6,020,677, entitled carbon cone and carbon whisker field emitters, discloses carbon structures formed via ion beam bombardment and ion beam doping of carbon for improved emission. The entire contents of U.S. Pat. Nos. 6,020,747; 6,146,227; 6,239,547; 6,020,677 are hereby expressly incorporated by reference herein for all purposes.

The invention can include an array of individually electrically addressable, high aspect ratio fibers (e.g., VACNFs) that are located either on an insulating substrate or a (semi)conductive substrate that has been coated with an insulating layer. The invention can include methodology for fabricating the individually electrically addressable, vertically aligned carbon nanofiber (VACNF) arrays. The VACNFs can be grown with DC plasma enhanced CVD. The use of the DC plasma requires a bias between the substrate which is located on a cathode and an anode located in a deposition chamber. Therefore, the substrate and/or its associated layers that are present when the DC plasma enhanced CVD is performed should be at least partially electrically conductive.

The invention can include arrays of fibers that can be used in a variety of applications including patterned cathodes for field emission (FE) devices and electrochemical probes suitable for the characterization of biological phenomena. These arrays can be fabricated with or without an insulating layer (electrochemical passivator) along the interconnects and sidewalls of the VACNF, allowing nanoscale control over the electrically or electrochemically active surface area of the probe tips.

The invention can include a set of conductive interconnects that individually electrically contact the fibers. The interconnects can be photolithographically patterned from a thin film that is deposited either directly on an insulating substrate or on an insulating layer that coats a (semi) conductive substrate.

The invention can include deterministically passivating the VACNF sidewalls and interconnects, rendering them electrically and electrochemically insulated. The resulting arrays can include individually electrically addressable fibers having nanoscale electrochemically active probe tips with insulated sidewalls and interconnect structures. Thus, the invention can provide the ability to create a nanoscale electrochemically active probe site on the VACNF tip.

The VACNFs in these arrays can be nanoscale, needle-like carbon fibers with diameters of typically less than 30 nm and lengths typically ranging from approximately 0.5 to approximately 10 $\mu$m. However, the diameters can be larger if desired (e.g., up to approximately 300 nm), and smaller (e.g., down to approximately 3 nm, using post growth etching). The lengths can also be longer (e.g., to approximately 200 $\mu$m) or shorter (e.g., 0.05 $\mu$m). The invention is ideally suited for creating patterned cathodes for FE devices. It also has several advantages over traditional fabrication techniques for synthesizing electrochemical or microelectrophysiological probes. VACNF arrays may be implemented as multipoint electrochemical probes where traditional probes are limited to producing single measurement point devices. The extremely small diameter and high aspect ratios of the VACNF combined with the ability to deterministically pattern their growth, represents another significant advance. In biological cell-based applications, the VACNF tip diameter provides a probe that can possibly penetrate into living cells with much less damage to the cell, its cytoskeletal network, nucleus, and organelles than traditional microelectrodes. The diameter of the probes may also provide for much faster response time, and significant improvements in spatial resolution (500:1 versus a 1 micron for conventional probes). The ability to deterministically fabricate arrays of electrodes provides the ability to measure multiple points around a sample at known spacing and to potentially evaluate multiple chemical species with a single measurement array.

Any catalyst capable of producing VACNFs may be used in this process. Examples of suitable catalysts are nickel, iron, cobalt and alloys thereof. After fabrication of the fibers, it might be useful to remove the catalyst particle(s). The catalyst particle(s) can be removed by chemical etching (e.g., nitric acid) and/or plasma etching.

The interconnect structure can be made from any metal or combination of metals that survive the DC PECVD process used to grow the VACNFs. Since the interconnect structure may be subjected to sputtering and/or damage, soft materials such as Pt should be avoided. Further, since the interconnect structure may be subjected to high temperatures during the catalytic synthesis of the fibers, low melting point materials such as Al should be avoided. For instance, the interconnect structure may include one, or more, refractory metal(s) such as, for example, W, Mo, Ta, Nb and alloys thereof. The parallel leads for active capacitance cancellation can be made from the same, or different, material as the interconnects.

The buffer layer may be composed of any material that can be deposited conformally over the interconnect structure precursor layer. For instance, the buffer layer may include Ti, W, Mo, titanium nitride and combinations thereof.

The electrochemical passivation layer may be composed of any insulating thin film that can be deposited conformally over the VACNFs and interconnect structures. The passivation layer may include silica, silicon nitride and/or an insulating polymer.

Any anisotropic etching process that can be used to pattern the interconnect materials or the electrochemical passivation layer may be substituted into the fabrication process discussed for the present embodiment so long as it achieves similar results. Suitable etchant chemistries can be based on $CF_4:O_2$ and/or $CF_4:SF_6$.

The substrate used in this process can be composed of any (insulating, conductive or semiconductive) material that can be coated with conductive layer(s) that survive the DC PECVD process used to produce VACNFs. Examples may include wafers made of quartz, fused silica, sapphire or any other material that fits this description. The substrate can be substantially optically transmissive.

Arrays of probes with different element sizes may be fabricated using this process ranging from single element probe structures to N×M arrays, where N and M are arbitrary integers. For instance the array can be a 1×M array, which can be termed a comb, or a 100,000×100,000 array, which can be termed a brush.

Electrodes with multiple VACNFs may be prepared by patterning multiple growth sites on each electrode. Each site then gives rise to a fiber and the density of the fibers can be controlled and/or varied.

The invention can include providing, or activating, interconnects to less than all of the fibers. Although preferred embodiments of the invention include individually electrically addressable fibers, the invention can include interconnecting sets and/or subsets of fibers in parallel. In this way, subgroups of fibers can be arranged.

Electrodes with randomly grown arrays of VACNFs may be prepared by patterning large areas of catalyst that will break into numerous catalyst droplets during the annealing phase of the VACNF growth process.

The invention can include additional layers deposited on and/or over the array. For example, the invention can include providing a conductive layer, having apertures for the fiber tips, that is spaced apart from and substantially parallel to the substrate.

The invention can also be included in a kit. The kit can include some, or all, of the components that compose the invention. The kit can be an in-the-field retrofit kit to improve existing systems that are capable of incorporating the invention. The kit can include software, firmware and/or hardware for carrying out the invention. The kit can also contain instructions for practicing the invention. Unless otherwise specified, the components, software, firmware, hardware and/or instructions of the kit can be the same as those used in the invention.

The invention can also utilize data processing methods that transform signals from the structures undergoing fabrication to control the fabrication process. For example, the invention can be combined with instrumentation to obtain state variable information to actuate interconnected discrete hardware elements. For instance, the invention can include the use of electric field sensing instrumentation to control the etch stop on the passivator.

The terms a or an, as used herein, are defined as one or more than one. The term plurality, as used herein, is defined as two or more than two. The term another, as used herein, is defined as at least a second or more. The terms including and/or having, as used herein, are defined as comprising (i.e., open language). The term coupled, as used herein, is defined as connected, although not necessarily directly, and not necessarily mechanically. The term approximately, as used herein, is defined as at least close to a given value (e.g., preferably within 10% of, more preferably within 1% of, and most preferably within 0.1% of). The term substantially, as used herein, is defined as at least approaching a given state (e.g., preferably within 10% of, more preferably within 1% of, and most preferably within 0.1% of). The term deploying, as used herein, is defined as designing, building, shipping, installing and/or operating. The term means, as used herein, is defined as hardware, firmware and/or software for achieving a result. The term program or phrase computer program, as used herein, is defined as a sequence of instructions designed for execution on a computer system. A program, or computer program, may include a subroutine, a function, a procedure, an object method, an object implementation, an executable application, an applet, a servlet, a source code, an object code, a shared library/dynamic load library and/or other sequence of instructions designed for execution on a computer system.

EXAMPLE

A specific embodiment of the invention will now be further described by the following, nonlimiting example which will serve to illustrate in some detail various features. The following example is included to facilitate an understanding of ways in which the invention may be practiced. It should be appreciated that the example which follows represents an embodiment discovered to function well in the practice of the invention, and thus can be considered to constitute the best mode for the practice of the invention. However, it should be appreciated that many changes can be made in the exemplary embodiment which is disclosed while still obtaining like or similar result without departing from the spirit and scope of the invention. Accordingly, the example should not be construed as limiting the scope of the invention.

Figures 1A, 1B, 1C, 1D, 1E:
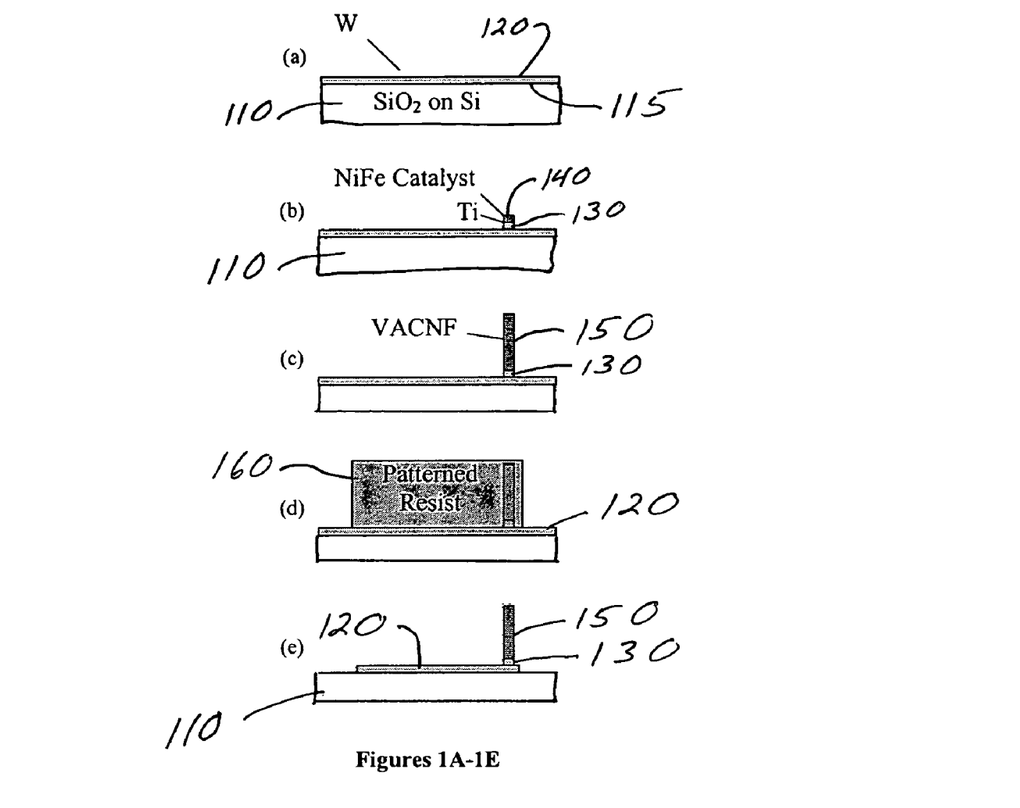
FIGS. 1A–1E illustrate schematic views of a summary of a fabrication process, representing an embodiment of the invention.

An exemplary fabrication process is summarized in FIGS. 1A–1E. In FIG. 1A, a silicon substrate 110 with an insulating silica surface 115 is coupled to a tungsten interconnect layer 120. In FIG. 1B, a titanium buffer layer 130 is coupled to the interconnect layer 120. A nickel iron alloy catalyst layer 140 is coupled to the buffer 130. This catalyst layer may break up into smaller droplets during an anneal phase. Once the catalyst droplets form, they can be termed particles as each droplet may behave as a single particle. In FIG. 1C, a substantially vertically aligned carbon nanofiber 150 has been grown. One end of the nanofiber 150 is connected to the buffer layer 130. The catalyst particle which rides on the top of the growing nanofiber 150 has been removed in FIG. 1C. In FIG. 1D, a patterned photoresist 160 has been developed. In FIG. 1E the photoresist 160 and those portions of the interconnect layer 120 that were not protected by the photoresist 160 have been removed.

The substrates used to fabricate the present embodiment are 3-inch Si wafers that have been thermally oxidized to form a 1.8 $\mu$m passivating layer of $SiO_2$. A 500 Å thick layer of W is deposited onto the wafer by RF sputtering in a vacuum chamber with a base pressure of $10^{-6}$ torr. The wafers are then coated in positive tone electron beam sensitive resist. A bilayer of two different molecular weight (MW) polymers is used to facilitate liftoff pattern transfer. For the bottom layer, a 4% 450K MW polymethyl methacrylate (PMMA) in anisole is spin cast onto the substrates at 4000 rpm for 1 minute. This is followed by a 15 minute curing step at 170° C. performed on a hotplate in room ambient. The upper layer consists of a 2% 950K MW PMMA in methyl isobutyl ketone (MIBK) deposited onto the first layer and spin cast at 2000 rpm. Following an additional curing step identical to the one described above, the wafers are loaded into an electron beam lithography (EBL) system—the EBL system used in this work was a Leica VB6-HR operated at an accelerating voltage of 100 keV and a beam current of 1 nA. The exposed pattern consisted of a 2×2 array of 50-nm dots that served as the catalyst sites for VACNF growth and alignment marks for subsequent lithography steps. The wafers are exposed with a 3×3 array of this pattern forming nine discrete die, where each die is separated from each other by 15 mm in both x and y. The exposures are developed in a solution of MIBK: isopropanol 1:3 for 1 minute, rinsed in isopropanol and blown dry with $N_2$. The use of two different MW PMMA creates a reentrant profile in the developed resist sidewalls allowing metals films deposited by PVD to cleanly lift off. Following inspection in an optical microscope the patterns are metallized using a liftoff technique. 100 Å of Ti followed by 100 Å of NiFe alloy (50/50) is deposited by electron gun PVD onto the wafers in a vacuum chamber with a base pressure of $10^{-6}$ torr. The coated wafers are then immersed in beakers containing acetone for 1 hour. The acetone dissolves the unexposed resist, removing the metal from the unpatterned areas of the substrate to leave behind a positive metal image of the exposed pattern. To ensure that the surface of the substrate is free from any metallic debris, the substrates are kept in the acetone containing beakers and placed in an ultrasonic agitator for 30 sec. The substrates are then removed from the acetone while being sprayed with isopropanol and are then blown dry with $N_2$ (FIG. 1–b).

Using electron gun PVD, a 1000 Å layer of Ti is deposited onto the backside of the wafer to allow electrical contact between this side and the front of the wafer. Before placing the substrates into the glass chamber of the DC PECVD system used to grow the VACNFs, the edges of the wafers are protected with a Ta foil to ensure that electrical contact is maintained during the growth process. Electrical contact to both sides of the wafer and the heater platen is an essential part of this growth process. After fixing the wafer to the heater with a conductive silver paint, the chamber is evacuated with a mechanical pump to a base pressure less than 5 mtorr.

Prior to VACNF growth the substrates were etched in ammonia plasma at 350° C. and then annealed at 700° C. to 750° C., the temperature at which VACNFs are typically grown. Previous work has shown that an initially continuous catalyst film, nominally 20 nm thick, breaks into submicron droplets during this annealing phase. For circularly patterned catalyst sites, the diameter of the patterned area and the thickness of the catalyst determine whether multiple or single droplets form during the annealing. By restricting the diameter, a single catalyst droplet forms. This droplet is the necessary precursor for the catalytic growth of single VACNFs at the lithographically predetermined locations.

A mixture of carbonaceous and etchant source gases are used for the VACNF growth. In the present work, acetylene and ammonia were used. The etchant is needed to remove the graphitic C film that continuously forms during the growth from the plasma discharge, passivating the catalyst and thereby preventing the formation of VACNFs. To initiate the VACNF growth process the ammonia-helium mixture is introduced into the chamber first and a DC plasma discharge is created. After the plasma is started, acetylene is introduced and the VACNF growth begins. Each catalyst droplet initiates the formation of an individual VACNF, riding upward on the tips of the VACNFs providing continued catalytic growth. The VACNFs are aligned along the direction of the electric field in the plasma discharge and normally grow perpendicular to the substrate (see FIG. 1C).

The wafers are then spin coated in 1 $\mu$m of i-line photoresist (Olin OiR 620-7i) and the pattern for the probe interconnects are exposed using a brightfield mask on a GCA Autostep200 5× reduction stepper. This system is capable of exposing patterns with less than 50 nm of overlay mismatch between pre-existing exposures on the Leica VB6 as demonstrated by some of the authors previously. The wafers are subjected to a post exposure bake at 115° C. for 1 minute and then developed in MF 321 developer (0.021N tetramethyl ammonium hydroxide in deionized water) for 1 minute rinsed in deionized water and then blown dry in $N_2$ (see FIG. 1D).

To transfer the electrode pattern into the W layer the wafers are placed in a reactive ion etch and subjected to an RF $CF_4:O2$ (20 sccm:1 sccm) plasma for 2 minutes. The chamber is operated at a base pressure of 50 mtorr with a plasma power density of 0.25 W/cm2 (see FIG. 1E). These conditions etch W at a rate of roughly 30 nm a minute. Following the etching, the wafers are removed from the chamber and immersed in acetone to remove the remaining photoresist.

Figure 2:
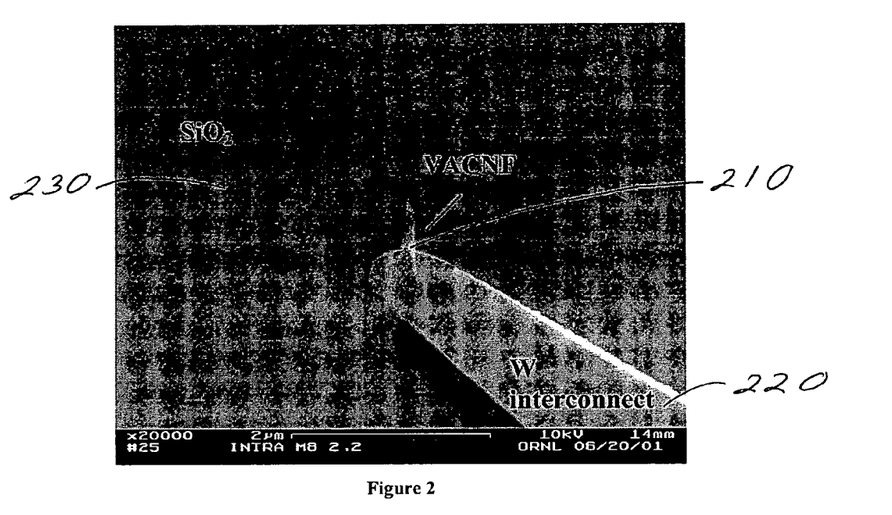
FIG. 2 illustrates a view of a SEM micrograph of a VACNF contacted by a W electrode on an $SiO_2$ substrate taken at 45°, representing an embodiment of the invention.

The cleaned wafers are inspected in a scanning electron microscope (SEM) and an example micrograph of the result is shown in FIG. 2. In FIG. 2, a VACNF 210 is shown standing at the end of a W interconnect 220 that is located on a silica insulating surface 230. FIG. 2 proves that the invention works.

Figures 3A, 3B, 3C, 3D, 3E:
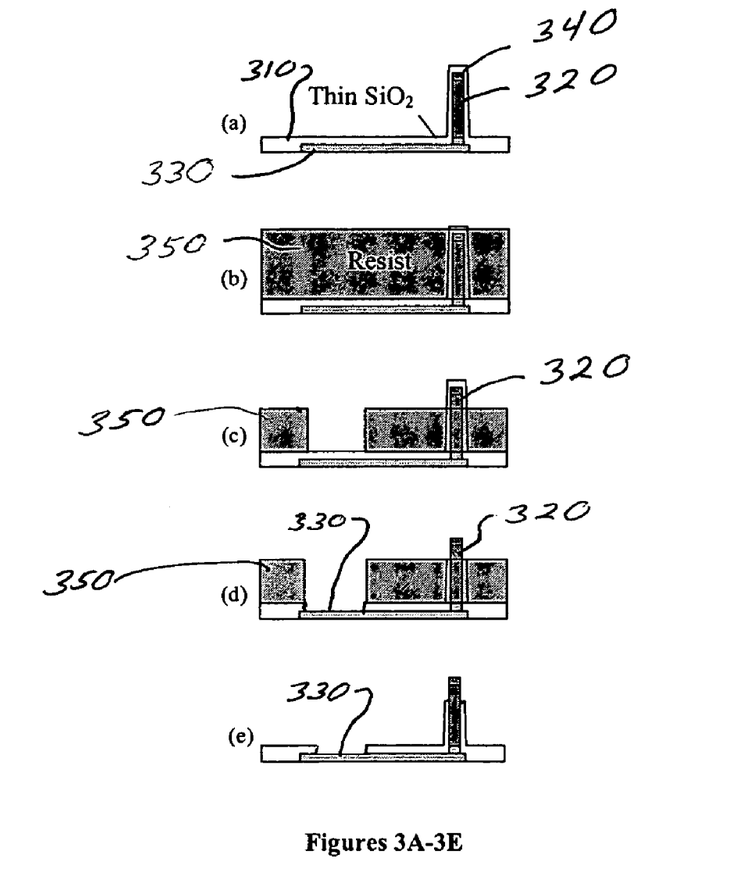
FIGS. 3A–3E illustrate schematic views of a summary of a tip passivation process, representing an embodiment of the invention.

An exemplary passivation process is summarized in FIGS. 3A–3E. In FIG. 3A, a thin layer of silica 310 has been deposited as an electrochemical passivator over a VACNF 320 and an interconnect 330. A nickel iron alloy catalyst particle 340, which has not been removed, is shown on the top of the VACNF 320. In FIG. 3B, a photoresist 350 has been coated over the silica 310. In FIG. 3C, the photoresist has been developed and rinsed to expose the top of the silica coated VACNF 320 and a portion of the silica coated interconnect 310. In FIG. 1D, the exposed silica has been etched away through the patterned photoresist 330, thereby exposing the VACNF 320 and the interconnect 330. In FIG. 1E the photoresist 330 has been removed.

To passivate the sidewalls of the fibers and the surface of the electrode interconnects a 50-nm thick layer of $SiO_2$ is deposited onto the substrates using a silane-based PECVD process. This process creates a conformal oxide covering suitable for this application (see FIG. 3A). The probes are coated in a layer of photoresist, spun onto the substrates as described above (see FIG. 3B). A darkfield mask with an array of rectangles aligned to the bonding pads of the interconnects is then exposed and developed as described above. The wafers are then placed in an RIE chamber and then etched in an $O_2$ plasma (30 sccm) for approximately 1 minute or until the photoresist is removed from the tips of the fibers. The thickness of the resist and the etch process can be tuned to provide nanometer-level control over length of the exposed VACNF tip (see FIG. 3C). This etch process is followed immediately by a $CHF_3:O2$ (30 sccm:1sccm) plasma for 2 minutes or until the oxide is removed from the surface of the VACNF tips and the W probing pads (see FIG. 3D). Both plasmas are operated at a chamber pressure of 30 mtorr and a power density of 0.25 W/cm2. Finally, the resist is removed from the wafers by immersing them in acetone and then ultrasonically agitating them for 30 sec (see FIG. 3E). To ensure that all chemical residue is removed from the electrochemically active VACNF tips, the substrates can be subjected to a brief, low power $O_2$ plasma.

Figure 4:
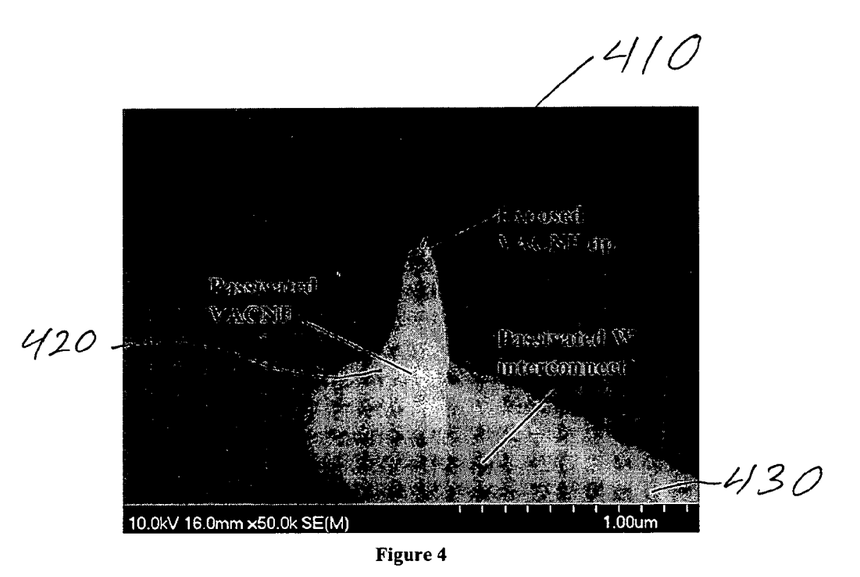
FIG. 4 illustrates an SEM micrograph of a VACNF probing device with $SiO_2$ passivated fiber sidewalls and interconnects taken at 45°, representing an embodiment of the invention.

An SEM micrograph of a completed nanofiber probe tip is shown in FIG. 4. An exposed VACNF tip 410 can clearly seen at the apex of the passivated VACNF 420. It can be appreciated that the electrochemical passivation coating is contiguous between the VACNF and the tungsten interconnect 430.

Figure 5:
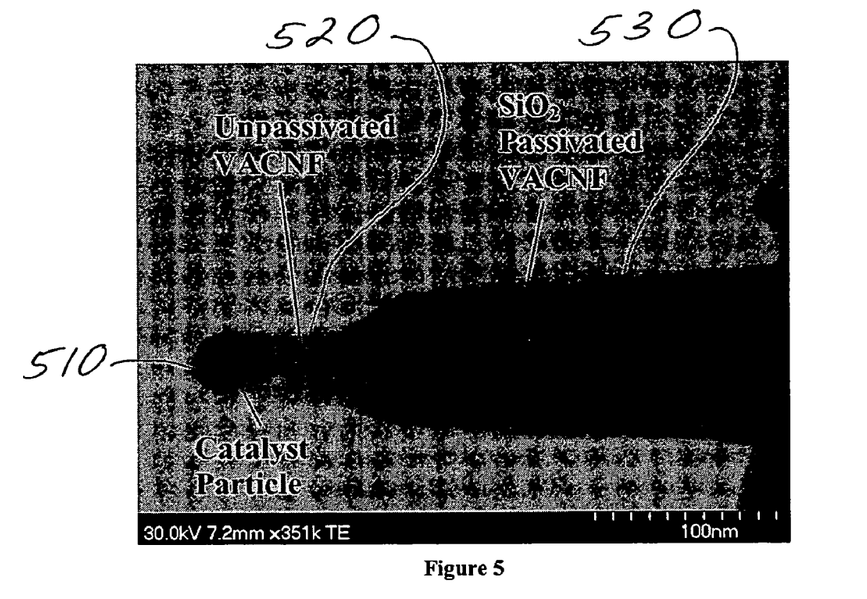
FIG. 5 illustrates an STEM micrograph of a VACNF probing device with $SiO_2$ passivated fiber sidewalls and interconnects, representing an embodiment of the invention.

A scanning transmission electron microscope (STEM) micrograph of an oxide passivated VACNF with an exposed tip is shown in FIG. 5. A catalyst particle 510 can be seen within the tip of an unpassivated portion 520 of the VACNF which extends from the passivated portion 530 of the VACNF.

Figures 6A, 6B, 6C:
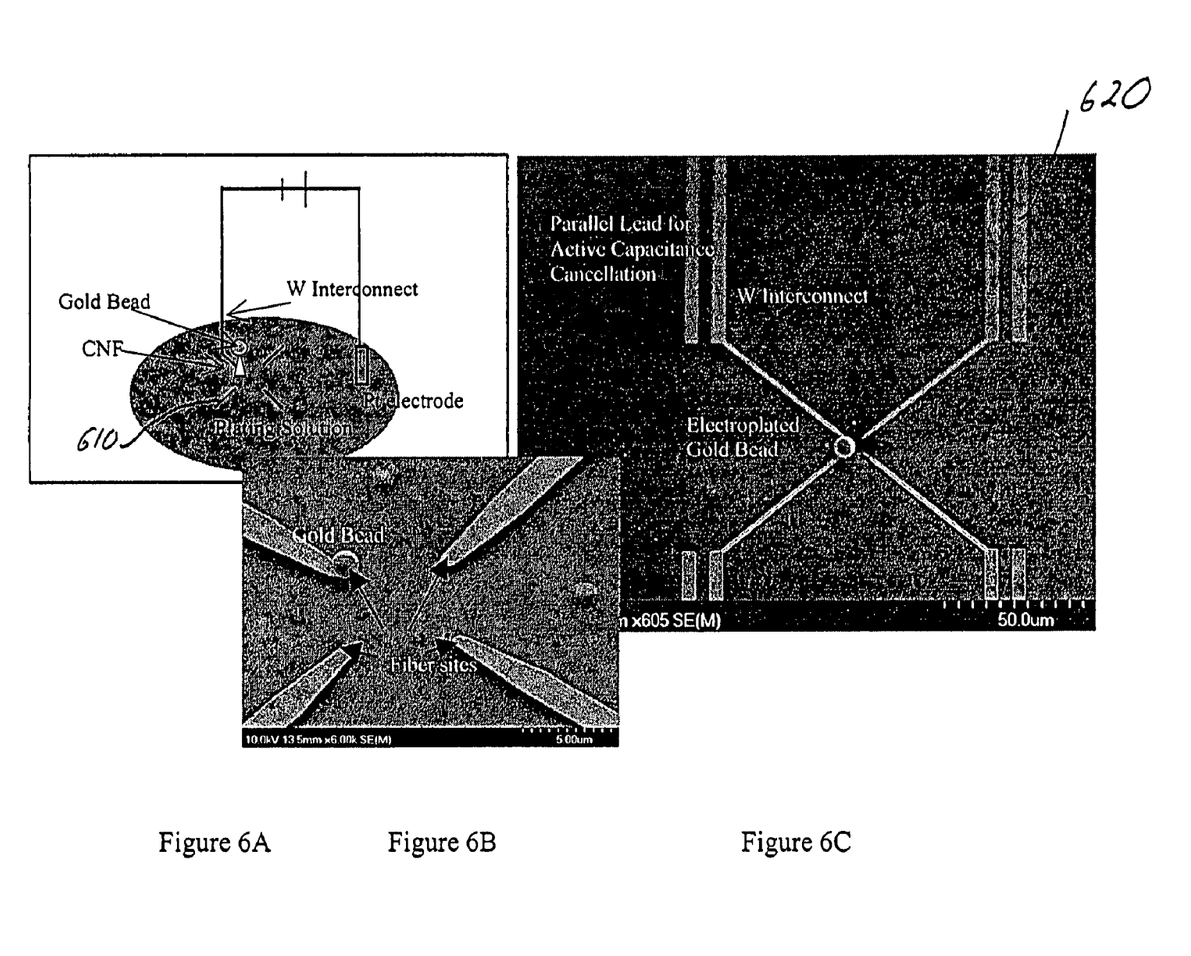
FIGS. 6A–6C illustrate a demonstration of the electrochemical activity of probes by electroplated deposition of gold at electrochemically active sites where, on two separate arrays (FIGS. 6B and 6C) gold deposition occurred at the exposed carbon fiber site at the terminus of a silicon dioxide passivated tungsten interconnect, representing an embodiment of the invention.

FIG. 6A shows a schematic view of an apparatus for testing the invention. FIGS. 6B–6C provides electron micrographs of two separate, 4-element, fibered arrays prepared using this fabrication methodology. Fiber elements are located at the terminals of 4 tungsten interconnects 610 that are separated from one another by a distance of approximately 1 micron. Tungsten interconnects provide individual electrical addressability of each fiber via contact pads at the periphery of the chip. An additional tungsten lead 620 is patterned parallel to each tungsten interconnect to enable active capacitance cancellation for high-speed, electrochemical measurement techniques.

To demonstrate the electrochemical activity of individual fiber probes, one fiber element of each 4-element array was interconnected to measurement/control electronics via tungsten interconnects to contact pads at the periphery of the chip. Approximately 10 microliters of gold electroplating solution [Technic Orotherm HT Gold Solution, Technic, Cranston R.I.] was applied to the chip surface, covering the fiber array and most of the surface area above the underlying tungsten electrodes, but not extended to the contact pad location at the periphery of the chip. A 20 mil platinum wire was immersed into the droplet as a reference electrode. A low noise current preamplifier [Stanford Research Systems, Model SR570] was used to apply −1.5V (wrt Pt electrode) to the tungsten interconnect of a single fiber element of two separate arrays (figure inset diagram). One fiber element (inset micro graph) received deposition current of 4 nA for 1 sec forming a gold bead of 1.45 micron diameter at the fiber location. Another fiber element of a separate array received 4 nA deposition current for 300 sec, forming a 7.5 micron gold bead at the fiber location (figure right). The resulting deposition of gold was limited to the fiber location with little to no deposition along the tungsten interconnect. This indicates that the fiber location is electrochemically active and that the oxide passivation layer (covering the tungsten interconnects and substrate) is of high quality with little to no significant leakage current passing through the passivation layer.

PRACTICAL APPLICATIONS OF THE INVENTION

The invention can be used as patterned cathodes for FE devices. These devices may include, but are not limited to, electron sources for electron microscopy, electron beam lithography, vacuum micro- and nanoelectronic devices or FE flat panel display applications. The invention can be used in conjunction with electrical probing of surfaces for the purposes of electronic materials characterization. The invention can be used in conjunction with electrochemical determination of the concentration of molecular species at submicroscopic resolution. For instance, the invention can be used in conjunction with electrochemical determination of the concentration of molecular species to make this determination at material interfaces. The invention can be used to observe galvanic processes at submicroscopic resolution. The invention can be used to observe electrochemical species within and around living cells. The invention can be used to monitor the flux of chemical species between cells and cellular locales. The invention can be used to evaluate the influence of chemico-environmental stimuli on cells in real-time by observing chemical phenomena at submicroscopic resolution. The invention can be used to evaluate pharmacokinetic response of cells to such manipulations. For instance, the invention can be used to perform these evaluations at multiple points within and around measured systems. The invention can be used to perform multiple different measurements at multiple points within and around measured systems. There are virtually innumerable uses for the invention, all of which need not be detailed here.

All the disclosed embodiments of the invention disclosed herein can be made and used without undue experimentation in light of the disclosure. The invention is not limited by theoretical statements recited herein. Although the best mode of carrying out the invention contemplated by the inventor(s) is disclosed, practice of the invention is not limited thereto. Accordingly, it will be appreciated by those skilled in the art that the invention may be practiced otherwise than as specifically described herein.

Further, the individual components need not be formed in the disclosed shapes, or combined in the disclosed configurations, but could be provided in virtually any shapes, and/or combined in virtually any configuration. Further, the individual components need not be fabricated from the disclosed materials, but could be fabricated from virtually any suitable materials. Further, homologous replacements may be substituted for the substances described herein. Further, variation may be made in the steps or in the sequence of steps composing methods described herein. Further, although the individually electrically addressable fiber(s) described herein can be a separate module, it will be manifest that the fiber(s) may be integrated into the system with which it is (they are) associated. Furthermore, all the disclosed elements and features of each disclosed embodiment can be combined with, or substituted for, the disclosed elements and features of every other disclosed embodiment except where such elements or features are mutually exclusive.

It will be manifest that various substitutions, modifications, additions and/or rearrangements of the features of the invention may be made without deviating from the spirit and/or scope of the underlying inventive concept. It is deemed that the spirit and/or scope of the underlying inventive concept as defined by the appended claims and their equivalents cover all such substitutions, modifications, additions and/or rearrangements.

The appended claims are not to be interpreted as including means-plus-function limitations, unless such a limitation is explicitly recited in a given claim using the phrase(s) "means for" and/or "step for." Subgeneric embodiments of the invention are delineated by the appended independent claims and their equivalents. Specific embodiments of the invention are differentiated by the appended dependent claims and their equivalents.

What is claimed is:

1. An apparatus, comprising:
    a substrate including an insulating surface;
    a first individually electrically addressable electrically conductive interconnect directly connected to the insulating surface of the substrate;
    a first vertically aligned carbon nanofiber grown from the first individually electrically addressable electrically conductive interconnect;
    a second individually electrically addressable electrically conductive interconnect directly connected to the insulating surface of the substrate; and
    a second vertically aligned carbon nanofiber grown from the second individually electrically addressable electrically conductive interconnect,
    wherein the first vertically aligned carbon nanofiber is individually electrically addressable via the first individually electrically addressable electrically conductive interconnect and the second vertically aligned carbon nanofiber is individually electrically addressable via the second individually electrically addressable electrically conductive interconnect.

2. The apparatus of claim 1, further comprising the substrate, wherein the substrate includes at least one member selected from the group consisting of quartz, sapphire and magnesia.

3. The apparatus of claim 1, further comprising the substrate, wherein the substrate is substantially optically transmissive.

4. The apparatus of claim 1, wherein the electrically conductive interconnect includes at least one refractory metal selected from the group consisting of W, Mo, Ta and Nb.

5. The apparatus of claim 1, further comprising a parallel lead for active capacitance cancellation coupled to the electrically conductive interconnect, wherein the parallel lead and the electrically conductive interconnect define a plane that is substantially perpendicular to both the first vertically aligned carbon nanofiber and the second vertically aligned carbon nanofiber.

6. The apparatus of claim 1, further comprising a catalyst coupled to the at least one member selected from the group consisting of the first vertically aligned carbon nanofiber and the second vertically aligned carbon nanofiber.

7. The apparatus of claim 6, wherein the catalyst includes at least one metal selected from the group consisting of nickel, iron and cobalt.

8. The apparatus of claim 1, further comprising a buffer between the at least one member selected from the group consisting of the first vertically aligned carbon nanofiber and the second vertically aligned carbon nanofiber and at least one member selected from the group consisting of the first electrically conductive interconnect and the second electrically conductive interconnect.

9. The apparatus of claim 8, wherein the buffer includes at least one substance selected from the group consisting of Ti, W, Mo and titanium nitride.

10. The apparatus of claim 1, further comprising an electrochemical passivator deposited on at least a portion of a sidewall surface of at least one member selected from the group consisting of the first vertically aligned carbon nanofiber and the second vertically aligned carbon nanofiber.

11. The apparatus of claim 10, wherein the electrochemical passivator includes a dielectric layer including at least one member selected from the group consisting of $SiO_2$, $Si_3N_4$ and a polymer.

12. The apparatus of claim 10, wherein a tip of the at least one member is not passivated.

13. A biosensor, comprising
a substrate including an insulating surface;
a first individually electrically addressable electrically conductive interconnect directly connected to the insulating surface of the substrate;
a first vertically aligned carbon nanofiber grown from the first individually electrically addressable electrically conductive interconnect;
a second individually electrically addressable electrically conductive interconnect directly connected to the insulating surface of the substrate; and
a second vertically aligned carbon nanofiber grown from the second individually electrically addressable electrically conductive interconnect,
wherein the first vertically aligned carbon nanofiber is individually electrically addressable via the first individually electrically addressable electrically conductive interconnect and the second vertically aligned carbon nanofiber is individually electrically addressable via the second individually electrically addressable electrically conductive interconnect.

14. The biosensor of claim 13, further comprising an electrochemical passivator deposited on at least a portion of a sidewall surface of at least one member selected from the group consisting of the first vertically aligned carbon nanofiber and the second vertically aligned carbon nanofiber.

15. The biosensor of claim 14, wherein the electrochemical passivator includes a dielectric layer including at least one member selected from the group consisting of $SiO_2$, $Si_3N_4$ and a polymer.

16. The biosensor of claim 14, wherein a tip of the at least one member is not passivated.

17. A field emitting array, comprising
a substrate including an insulating surface;
a first individually electrically addressable electrically conductive interconnect directly connected to the insulating surface of the substrate;
a first vertically aligned carbon nanofiber grown from the first individually electrically addressable electrically conductive interconnect;
a second individually electrically addressable electrically conductive interconnect directly connected to the insulating surface of the substrate; and
a second vertically aligned carbon nanofiber grown from the second individually electrically addressable electrically conductive interconnect,
wherein the first vertically aligned carbon nanofiber is individually electrically addressable via the first individually electrically addressable electrically conductive interconnect and the second vertically aligned carbon nanofiber is individually electrically addressable via the second individually electrically addressable electrically conductive interconnect.

18. The field emitting array of claim 17, further comprising an electrochemical passivator deposited on at least a portion of a sidewall surface of at least one member selected from the group consisting of the first vertically aligned carbon nanofiber and the second vertically aligned carbon nanofiber.

19. The field emitting array of claim 18, wherein the electrochemical passivator includes a dielectric layer including at least one member selected from the group consisting of $SiO_2$, $Si_3N_4$ and a polymer.

20. The field emitting array of claim 18, wherein a tip of the at least one member is not passivated.

21. A kit, comprising:
a substrate including an insulating surface;
a first individually electrically addressable electrically conductive interconnect directly connected to the insulating surface of the substrate;
a first vertically aligned carbon nanofiber grown from the first individually electrically addressable electrically conductive interconnect;
a second individually electrically addressable electrically conductive interconnect directly connected to the insulating surface of the substrate; and
a second vertically aligned carbon nanofiber grown from the second individually electrically addressable electrically conductive interconnect,
wherein the first vertically aligned carbon nanofiber is individually electrically addressable via the first individually electrically addressable electrically conductive interconnect and the second vertically aligned carbon nanofiber is individually electrically addressable via the second individually electrically addressable electrically conductive interconnect.

22. The kit of claim 21, further comprising instructions.

23. The kit of claim 21, further comprising an electrochemical passivator deposited on at least a portion of a sidewall surface of at least one member selected from the group consisting of the first vertically aligned carbon nanofiber and the second vertically aligned carbon nanofiber.

24. The kit of claim 23, wherein the electrochemical passivator includes a dielectric layer including at least one member selected from the group consisting of $SiO_2$, $Si_3N_4$ and a polymer.

25. The kit of claim 23, wherein a tip of the at least one member is not passivated.

* * * * *